US008208996B2

(12) United States Patent
Meyer et al.

(10) Patent No.: US 8,208,996 B2
(45) Date of Patent: Jun. 26, 2012

(54) IMAGING OF POLARIZATION SCRAMBLING TISSUE

(75) Inventors: Scott A. Meyer, Livermore, CA (US); Xing Wei, Dublin, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 367 days.

(21) Appl. No.: 12/381,406

(22) Filed: Mar. 10, 2009

(65) Prior Publication Data

US 2009/0247862 A1 Oct. 1, 2009

Related U.S. Application Data

(60) Provisional application No. 61/070,535, filed on Mar. 24, 2008.

(51) Int. Cl.
*G01J 4/00* (2006.01)
*G01B 9/02* (2006.01)
*A61B 5/00* (2006.01)

(52) U.S. Cl. ........ 600/476; 600/407; 600/477; 356/364; 356/450; 356/477; 356/491

(58) Field of Classification Search ................. 600/476, 600/477, 478, 407; 356/364, 450, 477, 491
See application file for complete search history.

(56) References Cited

U.S. PATENT DOCUMENTS

| | | | |
|---|---|---|---|
| 6,522,407 B2 * | 2/2003 | Everett et al. ................. 356/364 |
| 6,549,283 B2 * | 4/2003 | Eckert ........................... 356/369 |
| 6,850,329 B2 * | 2/2005 | Tobiason et al. .............. 356/495 |
| 7,016,048 B2 | 3/2006 | Chen et al. |
| 7,286,227 B2 | 10/2007 | Zhou et al. |
| 7,290,882 B2 | 11/2007 | Collins et al. |
| 2005/0018201 A1 * | 1/2005 | de Boer et al. ............... 356/479 |
| 2007/0109554 A1 * | 5/2007 | Feldchtein et al. .......... 356/492 |
| 2007/0146632 A1 | 6/2007 | Chipman |
| 2007/0216909 A1 | 9/2007 | Everett et al. |
| 2007/0291277 A1 | 12/2007 | Everett et al. |
| 2008/0002152 A1 | 1/2008 | Collins et al. |
| 2009/0310083 A1 * | 12/2009 | Campbell et al. ............. 351/215 |

OTHER PUBLICATIONS

Polarization vision: a new sensory approach to image understanding. Wolf, Lawrence B. Image and Vision Computing vol. 15, Issue 2, Feb. 1997, pp. 81-93.*
E. Götzinger et al., "Retinal pigment epithelium segmentation by polarization sensitive optical coherence tomography," *Optics Express*, vol. 16, No. 21, Oct. 15, 2008, pp. 16410-16422.
C.K. Hitzenberger et al., "Segmentation of the retinal pigment epithelium by polarization sensitive optical coherence tomography," *Proc. of SPIE*, vol. 6847 (2008), pp. 684705-1 through 684705-4.
S. Jiao et al., "Jones-matrix imaging of biological tissues with quadruple-channel optical coherence tomography," *Journal of Biomedical Optics*, vol. 7, No. 3, Jul. 2002, pp. 350-358.

(Continued)

*Primary Examiner* — Brian Casler
*Assistant Examiner* — Phong K Huynh
(74) *Attorney, Agent, or Firm* — Morrison & Foerster LLP

(57) ABSTRACT

The present invention provides for the detection and display of polarization scrambling tissue without resolving the polarization state of the backscattered imaging beam. In one embodiment, we illuminate the tissue using two different polarizations. A first polarization determines a first image of high intensity while the second polarization determines a second image of low intensity. Comparison and combination of the first and second images determines tissue which scrambles the polarization in neighboring detection cells.

27 Claims, 3 Drawing Sheets
(1 of 3 Drawing Sheet(s) Filed in Color)

OTHER PUBLICATIONS

M. Pircher et al., "Retinal pigment epithelium pathologies investigated with phase resolved polarization sensitive optical coherence tomography," *Proc. of SPIE*, vol. 6138, pp. 613801-1-613801-5, (2006).

M. Pircher et al., "Depolarization effects in human tissue investigated with transversal PS-OCT," *SPIE-OSA* (2005), vol. 5861, pp. 58610K-1 through 58610K-5.

M. Pircher et al., "Human Macula Investigated In Vivo with Polarization-Sensitive Optical Coherence Tomography," *Investigative Ophthalmology & Visual Science*, vol. 47, No. 12, Dec. 2006, pp. 5487-5494.

J.M. Schmitt et al., "Cross-polarized backscatter in optical coherence tomography of biological tissue," *Optics Letters*, vol. 23, No. 13, Jul. 1, 1998, pp. 1060-1062.

J. Zhang et al., "Full range polarization-sensitive Fourier domain optical coherence tomography," *Optics Express*, vol. 12, No. 24, Nov. 29, 2004, pp. 6033-6039.

* cited by examiner

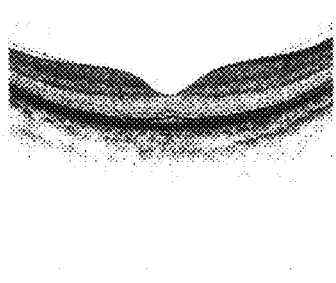
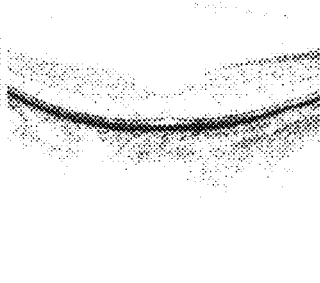
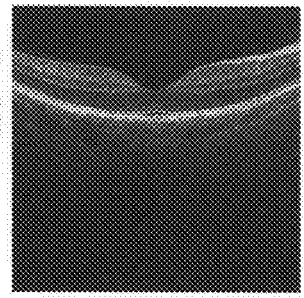
Fig. 5a　　　　Fig. 5b　　　　Fig. 5c
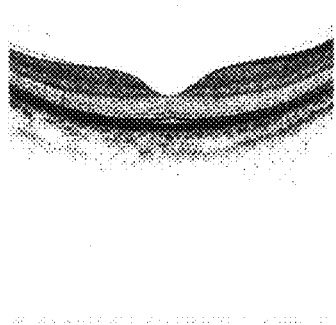
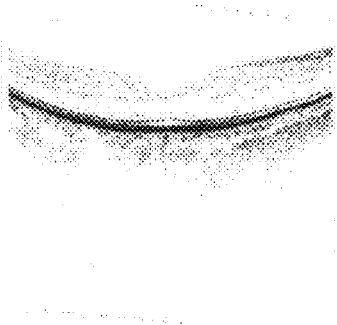
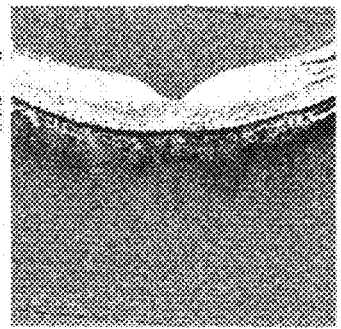
Fig. 6a　　　　Fig. 6b　　　　Fig. 6c

IMAGING OF POLARIZATION SCRAMBLING TISSUE

PRIORITY INFORMATION

This application claims priority from U.S. Provisional Application Ser. No. 61/070,535, filed Mar. 24, 2008, the disclosure of which is incorporated herein by reference.

TECHNICAL FIELD

The invention relates to the field of depolarization imaging. In particular, the invention pertains to optical imaging of polarization scrambling scattering tissue. It has particular relevance in optical coherence tomography (OCT).

DISCUSSION OF BACKGROUND

Pathology and disease states of the human eye lead to visual impairment and, in the worst case, loss of vision. Optical assessment of the eye's health is preferred because of the non-invasive nature of optical examination techniques. Common eye diseases include glaucoma, age-related macular degeneration, cataracts, retinal detachment, and diabetic retinopathy. Improved optical diagnostic techniques offer hope in quantifying disease progression and in tracking the effectiveness of disease treatments.

Previous work identifying depolarizing materials, alternatively called polarization scrambling materials, has largely focused on extracting information from the Mueller matrix. This work lies mainly in the field of polarimetry. It has been argued that, at least for optical coherence tomography (OCT), the Mueller calculus is not necessary. (See, S. Jiao and L. H. Wang, "Jones-matrix imaging of biological tissues with quadruple-channel optical coherence tomography," J. Biomed. Opt. 7(3), 350-358 (2002).) Depolarization is a consequence of analysis of incoherent scattering. Because OCT detection is coherent, depolarization, or polarization scrambling, by biological tissue simply means that the tissue does not present a spatially consistent polarization response across independent neighboring detection cells. In other words, the polarization state of the scattered light varies from detection cell to detection cell, whenever the detection cells are separated by more than the diameter of a speckle cell. Thus, in coherent detection devices like OCT, the degree of polarization is meaningful only when examining clusters of detection cells spanning a number of speckle diameters.

Alternatively, depolarization is directly addressed within the Mueller calculus. While the Mueller calculus nominally describes incoherently detected light, conversion from a Jones matrix to a Mueller matrix is possible and well-known (See, for example, Appendix 4: Jones-Mueller Matrix Conversion of "Spectroscopic Ellipsometry" by Hiroyuki Fujiwara (2007). Coherent detection is described by a subset of Mueller matrices. The full Mueller matrix contains information on the intensity, retardance, diattenuation, and depolarization of a scattering material. Evaluating the Mueller matrix on a scatterer-by-scatterer basis provides this information for each scatterer. In general, however, it is impractical to resolve each scatterer. In a typical OCT system, the resolution of the illumination beam (the detection cell) is specified to be nearly the same size as a speckle cell. In this case, computing or averaging the Mueller matrix over multiple speckle diameters, where each detection cell covers a plurality of actual scatterers is generally more practical. Nominally, for Mueller matrix imaging, the Mueller matrix is obtained on a pixel-by-pixel basis for a given image size. The 4×4 Mueller matrix has 16 real elements, and complete resolution of the Mueller matrix implicitly resolves the depolarization elements of the matrix.

The Mueller matrix elements for a scattering tissue represent the relationship between the input and the output Stokes vectors through the equation: $\hat{S}=MS$, where S is the Stokes vector representing the input beam, M is the Mueller matrix, and $\hat{S}$ is the Stokes vector representing the beam backscattered by the tissue. By illuminating the tissue with light of various known polarization states and computing the Stokes vectors of the backscattered light for each pixel of illuminated tissue, evaluation of the Mueller matrix for each pixel of illuminated tissue is possible.

The degree of polarization (DOP), $\mathcal{P}$, of light is the proportion of completely polarized light when the light is decomposed into a completely depolarized component and a completely polarized component. When light represented by Stokes vector, S, is decomposed into its completely polarized component, $S_P$, and its completely depolarized component, $S_D$, the DOP satisfies: $S=(1-\mathcal{P})S_D+\mathcal{P}S_P$. For Stokes vector $$S = \begin{pmatrix} S_0 \\ S_1 \\ S_2 \\ S_3 \end{pmatrix}$$

the DOP satisfies $\mathcal{P}=\sqrt{S_1^2+S_2^2+S_3^2}/S_0$.

The classical measure of the degree of depolarization imparted by a scattering medium is the depolarization index of the Mueller matrix M defined by Gil and Bernabeu:

$$D(M) = \frac{1}{\sqrt{3}} \frac{1}{m_{00}} \sqrt{\sum_{(i,j)\neq(0,0)} m_{ij}^2},$$

where $m_{ij}$ is the $(i,j)^{th}$ element of M. (See 20070146632 Chipman, Eq. 14). The depolarization index varies between zero and one. It is zero for the ideal depolarizer and one for non-depolarizing Mueller matrices. Once the Mueller matrix is known, the depolarization elements (the 9 Mueller matrix elements $m_{ij}$ for $i,j \geq 1$) are known and a depolarization image can be constructed.

In "Segmentation of the retinal pigment epithelium by polarization sensitive optical coherence tomography," Hitzenberger, et al., reported an alternate method for determining if tissue is depolarizing. Using a polarization sensitive OCT (PS-OCT) system with a polarizing beam splitter in the detection arm and two identical detection systems, they detected retardance data at each detection cell. Polarization preserving tissue returns consistent retardation values from neighboring scatters, while depolarizing tissue returns randomly varying retardation values from neighboring scatters. By computing statistics on retardation measurements in a neighborhood of a pixel, Hitzenberger determines that the tissue is depolarizing at any location where the variance of the retardation measurements exceeds a fixed threshold. In other words, the greater the variance in the retardation measurements, the greater the depolarizing nature of the scattering tissue.

Full resolution of the Mueller or Jones matrix is costly and/or time consuming. A typical PS-OCT system requires at least a polarizing beamsplitter and two detection channels to evaluate the polarization state of the return light (from which retardation and other polarization parameters can be derived) and depolarizing tissue can be located using statistics as shown by Hitzenberger. In this case, the cost is in additional hardware. Additionally, a PS-OCT system is relatively difficult to align and calibrate. Our invention resolves these problems by estimating the location of polarization scrambling tissue without resolving the Mueller or Jones matrix (i.e. without resolving the actual polarization state of the light) or adding additional hardware to the detection channels of a typical OCT system.

SUMMARY

The claims define the present invention and nothing in this section should be taken as a limitation on those claims. Advantageously, embodiments of the present invention overcome the computational complexity and/or expensive detection hardware previously used in the art. The invention provides a means for imaging polarization scrambling tissue (alternatively called depolarization imaging herein) without resolution of Stokes vectors or the Mueller matrix and without the need of additional detection hardware.

One embodiment of the present invention is a method for displaying polarization scrambling tissue without resolving the polarization state of the sample beam.

Another embodiment of the present invention is a method for displaying polarization scrambling tissue by modulating a display image by a degree of depolarization parameter. This modulation may be by color or intensity. It may be linear or non-linear.

Yet another embodiment is a method of rapidly acquiring a 3-D volume image emphasizing depolarizing tissue.

BRIEF DESCRIPTION OF THE DRAWINGS

The patent or application file contains at least one drawing executed in color. Copies of this patent or patent application publication with color drawing(s) will be provided by the Office upon request and payment of the necessary fee

FIG. 5 shows an example of a color image of a depolarizing tissue measurement performed using an embodiment of the invention.

FIG. 6 is a schematic illustration of a polarization paddle.

DETAILED DESCRIPTION

Figure 1:
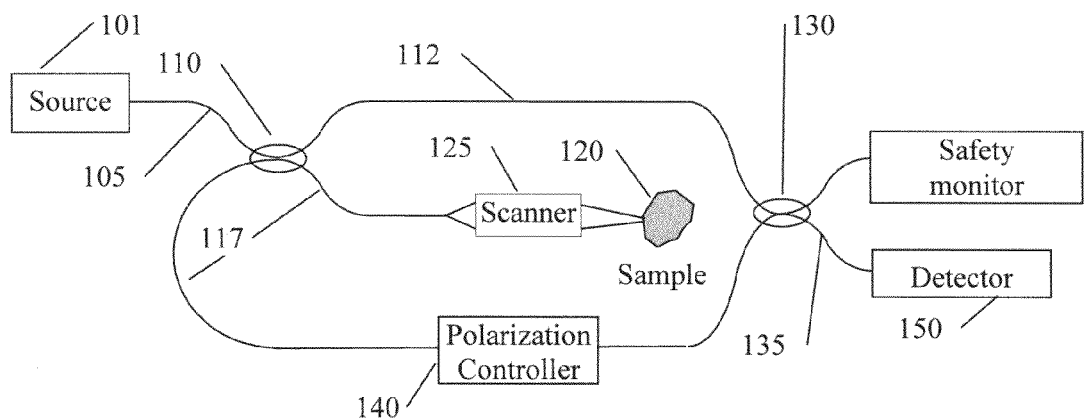
FIG. 1 is a schematic illustration of a Mach-Zehnder interferometer for OCT scanning.

The embodiments, examples and descriptions illustrate the principles of the invention and its practical applications and are not a definition of the invention. Modifications and variations of the invention will be apparent to those skilled in the art. The claims define the scope of the invention and include known equivalents and equivalents unforeseeable at the time of filing of this application.

One embodiment of the invention is an apparatus for computing a tomographic image of a depolarizing tissue. One such apparatus includes an optical coherence tomography (OCT) device comprising of an interferometer like the one depicted in FIG. 1 having a source arm 105, a reference arm 112, a sample arm 117 (here shown in two parts since the splitting coupler 110 and combining coupler 130 are separate and distinct) and a detector arm 135. A source 101, typically a superluminescent diode (SLD), of at least partially spatially coherent light is coupled to the source arm 105. A polarization controller 140, capable of varying the polarization state of light within a limited range, is coupled to the sample arm 117 of the interferometer. The sample 120 is scanned with light via scanner 125 and light returned from the sample arm interferes with light from the reference arm in coupler 130. The interference is detected 150, forming first intensity data. Intensity data may be detected using either time domain techniques or frequency domain techniques.

Typically, the Z-axis is chosen along the beam-line of the optical illumination. Data acquired along a beam-line is often referred to as an A-scan. The scanner 125 causes the beam-line to vary transversely. The transverse directions are generally called X and Y, though their relative orientation and location depending upon the choice of orientation of the Z-axis and the location chosen for the origin.

Figure 2:
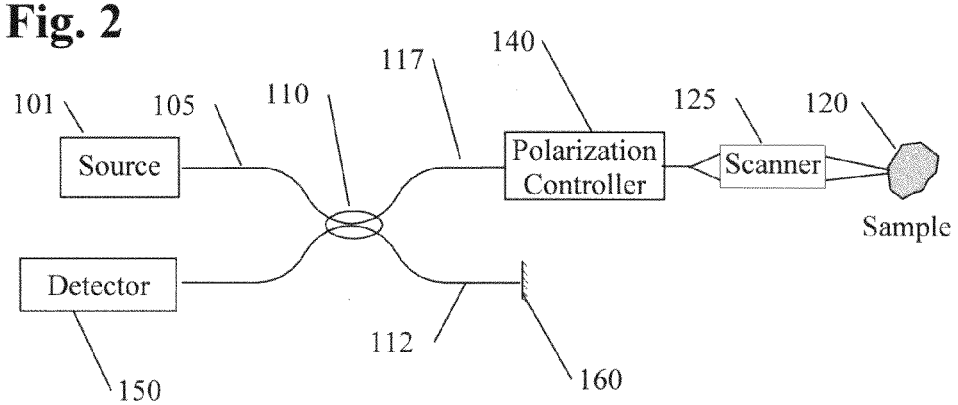
FIG. 2 is a schematic illustration of a Michelson interferometer for OCT scanning.

While the interferometer of FIG. 1 is a Mach-Zehnder transmissive reference arm architecture, the interferometer could also be a Michelson architecture, shown in FIG. 2. The Michelson architecture replaces the transmissive reference arm with a reference arm with reference reflector 160. The OCT system containing the interferometer should acquire data rapidly. A frequency domain OCT system is preferred. A frequency domain system may be either a spectral domain system, including a wide-band illumination source and a spectrometer, or a swept source system wherein narrowband frequencies are swept across the frequency band. For example, the spectral domain OCT system described in U.S. patent application Ser. No. 11/820,773, filed Jun. 20, 2006 (publication 2007/00291277) and incorporated herein by reference can be readily modified to support this invention.

As an alternative to varying the polarization in the sample arm 117, the polarization can be varied in the reference arm 112 by moving the polarization controller from the sample arm to the reference arm.

Figure 3:
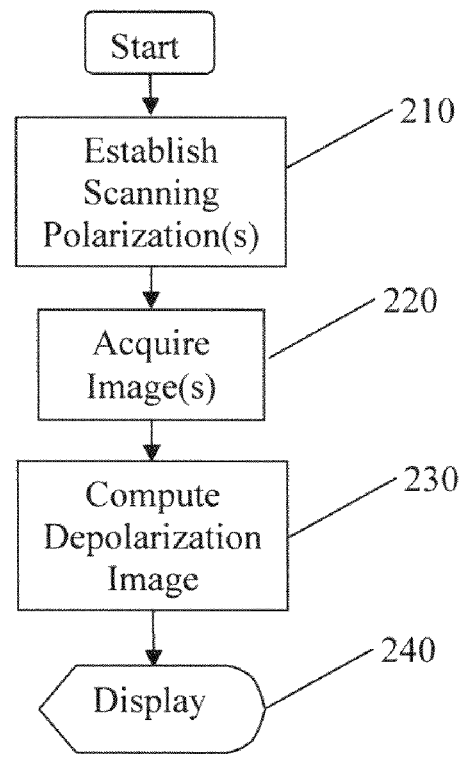
FIG. 3 is a flow diagram of the process steps for creating an image of depolarizing tissue.

In one embodiment, the tissue is illuminated twice and the Polarization Controller is set to impart two different polarizations on light passing through it. In this case, as depicted in FIG. 3, we first establish two polarizations 210. In one embodiment, we illuminate the tissue using a sequence of polarizations and determine the polarizations which create a maximum and minimum in the total intensity signal. We then acquire first and second images 220 using the polarizations which achieved the maximum and minimum intensities. When scanning can be performed quickly enough, the number of scans performed with uniquely different polarization states can be large, on the order of 25, 50 or even more different polarizations. However, when scanning time is limited, the number of trial scans with different polarization states may need to be kept quite small. In the latter case, the number of scans at different polarization states can be as small as 4 or 5. It should be appreciated that when the number of scans is smaller, the variation in polarization state for each scan should likely be larger than if a large number of scans can be accommodated. Comparison and combination of the first and second image intensity signals 230 enables detection of the depolarizing tissue. Optionally, this image is displayed 240 or stored (not shown).

In one embodiment, the same tissue is scanned to establish the two polarizations intended to be used in scanning for the final depolarization image. For example, if the depolarization image sought is a B-scan of a region of the eye and the total intensity used to determine the maximum and minimum requires scanning the entire B-scan, then the images acquired in 220 are optimally saved during the procedure 210 used to establish the scanning polarizations. This is readily accomplished when, for each polarization used in procedure 210, the B-scan is acquired, its total intensity is computed and compared to the maximum and minimum previous total intensities of previous B-scans. If it is greater than the previous maximum, its intensity value becomes the new maximum intensity value and the image replaces the previous maximum intensity image. If it is less than the previous minimum, its intensity value becomes the new minimum intensity value and the image replaces the previous minimum intensity image. Alternatively, if the polarizations are established by scanning over a limited region, procedure 210 may quickly test a number of polarizations, choose two and then acquire images 200 in a completely separate procedure.

Figure 4:
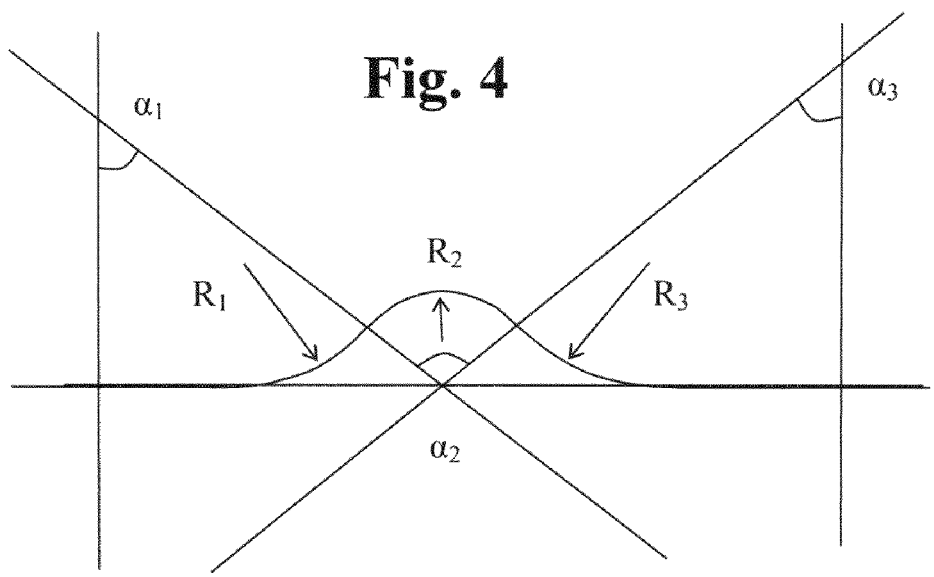
FIG. 4 is a schematic illustration of a polarization paddle.

In one embodiment, the polarization is varied over a sampled subset of all polarizations attainable by a single polarization paddle. The polarization paddle may be located in the sample arm or in the reference arm. As the polarization paddle is rotated, it imparts different polarizations on the light traveling through the fiber mounted on the paddle. In the representation of FIG. 4, a fiber would be mounted with a U-shape bend onto the paddle, but it could otherwise form the more traditional circular loop. The paddle can rotate out of the plane of the paper with the U-shape remaining in one plane at all times. The paddle design parameters are the three radii ($R_1$, $R_2$ and $R_3$) and the three angles ($\alpha_1$, $\alpha_2$, $\alpha_3$). These parameters are typically chosen to compensate for system birefringence.

In another embodiment, the polarization is varied over a sampled subset of all polarizations attainable by two or more polarization paddles. Alternatively, the polarization may be varied using a liquid crystal based polarization controller or an electro-optical polarization controller. Other polarization controllers with substantially similar operating parameters may be used, as will be clear to those versed in the art. In all cases, the polarizations are varied to determine the polarizations that establish detection efficiencies for the two images.

In another embodiment, the Establish Scanning Polarization process 210 of FIG. 3 is fixed in hardware. This hardware is a fast polarization modulator designed to rapidly vary the polarization to sample the scattering with a fixed number, say N, of detection efficiencies. This hardware may be placed in either the sample arm or the reference arm of the OCT interferometer. For example, this hardware may be a rotating retarder of N positions, for example a traditional ¼ lambda or ½ lambda rotating waveplate. Any polarization modulator that can produce a finite number of diversely varying polarization states where the polarization states are essentially fixed for each A-line may be used. Typically, N is less than 20 and preferentially it is between 2 and 6. Preferably the polarization is fixed or nearly fixed during acquisition of each A-line. Successive A-lines have different polarizations applied in the sample arm. While A-lines are normally quite closely spaced in typical OCT imaging, the A-lines can be oversampled or the same tissue may be imaged N times using a different polarization setting for each A-line acquisition. Preferentially, the A-lines are closely spaced. The acquired data 220 may be processed as N interleaved images, each acquired with a different polarization setting. From these N images, we select the maximum intensity image and the minimum intensity image from which to compute the depolarization image 230.

The system hardware may alternatively be placed in the reference path. Alternatively, a polarization paddle or other Polarization Controller may be placed in the reference arm. Advantageously, this paddle or controller may be varied to increase the variation between the maximum intensity image and the minimum intensity image. Preferably, this optimization is performed over a small region and then the polarization paddle is set for full image acquisition. This decreases the full image acquisition duration. However, when the total time of acquisition is not critical, the polarization paddle may be varied over the full image region to optimize its setting. The polarization paddle and the N polarization state fixed hardware may be in the same interferometer arm or in the alternate arms.

In yet another embodiment, a first polarization is a priori selected to be at or near the maximum for a population and a second polarization is a priori selected to be at or near the minimum for the same population. The a priori selection may be heuristically determined from a sample set, derived analytically from a model, or obtained by other means.

In one embodiment, the maximum intensity signal is the maximum intensity averaged over an entire B-scan. In this embodiment, the minimum intensity signal is the minimum intensity averaged over an entire B-scan. Alternatively, the maximum signal intensity may be determined by the average intensity over a region associated with a particular structural feature in the eye such as near the inner limiting membrane (ILM) within a B-scan. In this case, the B-scan is acquired for a particular polarization, the B-scan is segmented to locate the ILM, and the region near the ILM is identified before the signal intensity is computed. In this embodiment, the minimum intensity signal is also determined over the same region near the inner limiting membrane (ILM) within a B-scan by computing the average intensity over the region. In this case, the B-scan is acquired for a particular polarization, the B-scan is segmented to locate the ILM, and the region near the ILM is identified before the signal intensity is computed. In order to reduce the computation time, the B-scan may contain only a limited number of A-scans. Indeed, either method can be implemented using only a single, representative A-scan instead of the full B-scan.

If the maximum signal intensity is the maximum average intensity of a B-scan over all polarizations, then the minimum signal intensity is the minimum average intensity of a B-scan over all polarizations. Similarly, if the maximum signal intensity is the maximum average intensity near the ILM over all polarizations, then the minimum signal intensity is the minimum average intensity near the ILM over all polarizations. That is, the minimum signal intensity should be computed over the same or over nearly the same polarizations as the maximum and computed over the same or nearly the same regions of tissue as the maximum.

Preferentially, the images are scanned interleaved, to reduce or eliminate motion artifacts. However, it may be impractical to interleave the images. In this case, proper registration of A-lines between images reduces motion artifacts that distort the final image.

In one embodiment, the images are combined on a pixel-by-pixel basis. Let $I_{mn}^+$ represents the intensity of the (m,n) pixel of the image acquired using the polarization associated with the maximum intensity and $I_{mn}^-$ represents the intensity of the (m,n) pixel of the image acquired using the polarization associated with the minimum intensity. If $I_{mn}$ represents the total intensity and $I_{mn}^P$ represents the polarized intensity then the degree of polarization, $\mathcal{P}_{mn} = I_{mn}^P / I_{mn}$. Since, for perfectly correct polarization (i.e., where $I_{mn}^+$ contains all of the polarized intensity and ½ of the unpolarized intensity), $$I_{mn}^+ = I_{mn}^P + \frac{I_{mn} - I_{mn}^P}{2} = \frac{I_{mn} + I_{mn}^P}{2}$$

and, for perfectly orthogonal polarization (i.e. where $I_{mn}^-$ contains ½ of the unpolarized intensity)

$$I_{mn}^- = \frac{I_{mn} - I_{mn}^P}{2},$$

we have $$\mathcal{P}_{mn} = \frac{I_{mn}^+ - I_{mn}^-}{I_{mn}^+ + I_{mn}^-}.$$

Hence, we use the degree of depolarization, DOD, is $$DOD = 1 - \mathcal{P}_{mn} = \eta_{mn} = \frac{2I_{mn}^-}{I_{mn}^+ + I_{mn}^-}.$$

$\mathcal{P}_{mn}$ is a measure approaching 1 where the first and second image intensities are nearly equal and approaching 0 where the first image intensity is much larger than the second image intensity. If a single pixel is large enough that sufficiently many scatters are within an imaging cell (pixel), and then $\eta_{mn}$ represents the degree of depolarization for each pixel of an image. However, if each detection cell is sufficiently small that it represents a single scatterer or the imaging technique is coherently detected, then $\eta_{mn}$ should be computed using a smoothed $I_{mn}^+$ and $I_{mn}^-$, where smoothing is performed over a window sufficiently large to account for the number of scatterers needed to depolarize the incoming light. In particular, for OCT, where the detection is confocal and coherent and the detection cell is approximately the size of speckle, the image should be smoothed over a region sufficiently large to cover a statistically meaningful number of different speckle cells. That is, $$I_{mn}^+ = \sum_{\substack{|j-m|\le J \\ |k-n|\le K}} (w(j-m, k-n)\hat{I}_{mn}^+)$$

and $$I_{mn}^- = \sum_{\substack{|j-m|\le J \\ |k-n|\le K}} (w(j-m, k-n)\hat{I}_{mn}^-),$$

where w is a smoothing weight, $\hat{I}_{mn}^+$ and $\hat{I}_{mn}^-$ are the measured intensities, and J and K govern the size of the window. The weight w=1 simply pixel-wise averages the intensities. Windows with even length boundaries are also anticipated and readily understood by those versed in the art.

The DOD $\eta_{mn}$ can be used create a color image by modulating the Hue, Saturation, or Value of an HSV color representation of the image. For example, the Hue, Saturation, and Value may be set as a functions of $\eta_{mn}$, $I_{mn}^+$, and/or $I_{mn}^-$. In one instance, the Hue may be set to a function of $\eta_{mn}$ while the Saturation is saturated and the Value is set to a function of $I_{mn}^+$. FIG. 5 shows an example of a color image of depolarizing tissue. FIG. 5a is an image of tissue imaged with a polarization paddle set to achieve a near maximum intensity $I_{mn}^+$. In order to view the dynamic range, the image is essentially $\log(I_{mn}^+)$. FIG. 5a is displayed in reverse video, with high intensity shown in black and low intensity shown in white. FIG. 5b, also shown in reverse video, is the same tissue imaged with a polarization paddle set to achieve a near minimum intensity $I_{mn}^-$. FIG. 5c is a color representation of the depolarization image where the Hue is set to magenta, the Saturation is set to the degree of depolarization $$\eta_{mn} = \frac{2I_{mn}^-}{I_{mn}^+ + I_{mn}^-},$$

and the Value is set to the logarithm of $I_{mn}^+$.

Alternatively, the Hue may be set to a function of $\eta_{mn}$ while the Saturation is saturated and the Value may be set to a function of $I_{mn}^-$.

Alternatively, the intensity the image $I_{mn}$ can be used create a grayscale image. FIG. 6 shows an example of a grayscale image of depolarizing tissue. FIG. 6a is the same image as FIG. 5a. It shows tissue imaged with a polarization paddle set to achieve a near maximum intensity $I_{mn}^+$ in reverse video. FIG. 6b, also shown in reverse video, is the same as FIG. 5b. This is the same tissue imaged with a polarization paddle set to achieve a near minimum intensity $I_{mn}^-$. FIG. 6c is a grayscale modulation of the degree of depolarization with the image $I_{mn}^-$. A grayscale modulation may be computed as: $\tilde{I}_{mn}^+ = f(\eta_{mn})g(I_{mn}^+)$, or $\tilde{I}_{mn}^- = f(\eta_{mn})g(I_{mn}^-)$, or more generally $\tilde{I}_{mn} = h(I_{mn}^-, I_{mn}^+)$. Since $\eta_{mn}$ is likely very nearly 1 in regions of weak signal, $\eta_{mn}$ by itself enhances some noise. Modulation of $\eta_{mn}$ should maintain its strength where $I_{mn}^-$ is near its maximum, while reducing its strength where $I_{mn}^-$ is near its minimum. The normal image display for OCT is essentially logarithmic (in order to increase the dynamic range distinguishable by the human eye). FIG. 6c is an exemplary embodiment of the modulation $\eta_{mn} \log(I_{mn}^-)$. In general, while f and g may well be the identity function, it is preferred that g vary more slowly through values where $I_{mn}^-$ is rich in signal, such as a logarithmic function or even a step function, thresholded at a known noise level. A continuous function transitioning rapidly from nearly 1 above a threshold to nearly 0 below the threshold provides an alternative to a true step function. Various other modulations of color and grayscale representations are possible and will be appreciated by one versed in the art.

A tomographic image composed of A-line scans of enhanced regions of depolarizing tissue can be formed. In some instances, the metric $\tilde{I}_{mn}^- = f(\eta_{mn})g(I_{mn}^-)$ used to create a depolarizing tissue image is sufficiently dominated by $g(I_{mn}^-)$ that the image $I_{mn}^+$ is unnecessary for computing an approximate depolarizing tissue image $\check{I}_{mn}^- = g(I_{mn}^-)$. This is particularly useful when acquiring a 3-D volume of image data since, once the polarization is determined for imaging $I_{mn}^-$, whether this is done over a B-scan, a portion of a B-scan, or even over an A-scan, the entire 3-D volume can be acquired using only that fixed polarization. Thus, the depolarizing tissue image can be acquired rapidly and without scanning using a distinct second polarization.

When only two polarizations are used, it is obvious that there is only one scanning sequence: the sequence that is used to provide information about the depolarization of tissue. The preferred polarizations are already chosen. However, when the preferred polarizations need to be determined, there is a need for a scanning sequence to generate information needed to choose preferred polarizations (e.g. the polarizations which produce the maximum and minimum average intensity image information). This scanning sequence used for determining preferred polarizations need not be the same as the scanning sequence used to provide information about the depolarization of tissue. For example, the scanning sequence used to determine the best two polarizations might be the scanning sequence used to generate the lower resolution B-scans of U.S. Patent Publication 2007/0216909 while the scanning sequence used to generate the images from the chosen polarizations might be the high resolution scanning sequence of that patent Publication. In general, any appropriate sub-region of the region scanned by the scanning sequence used to provide information about the depolarization of tissue may be scanned to determine the preferred polarizations. In fact, even regions near the target region may be used to choose preferred polarizations, so long as the tissue is sufficiently uniform that the estimate obtained from the polarization choosing scans is relevant to the region scanned to provide information about the depolarization of the tissue.

It should be understood that the embodiments, examples and descriptions have been chosen and described in order to illustrate the principles of the invention and its practical applications and not as a definition of the invention. Modifications and variations of the invention will be apparent to those skilled in the art. The scope of the invention is defined by the claims, which includes known equivalents and unforeseeable equivalents at the time of filing of this application.

The following references are hereby incorporated herein by reference.

U.S. PATENT DOCUMENTS

2007/0216909 Everett et al., Methods for mapping tissue with optical coherence tomography data
2007/0291277 Everett et al., Spectral domain optical coherence tomography system
2007/0146632 Chipman, Advanced polarization imaging method, apparatus, and computer program product for retinal imaging, liquid crystal testing, active remote sensing, and other applications.
U.S. Pat. No. 7,286,227 Zhou, et al. Method and system for removing the effects of corneal birefringence from a polarimetric image of the retina
U.S. Pat. No. 7,016,048 Chen et al. Phase-resolved functional optical coherence tomography: simultaneous imaging of the stokes vectors, structure, blood flow velocity, standard deviation and birefringence in biological samples.

OTHER PUBLICATIONS

Zhang, J., et al. (2004). "Full range polarization-sensitive Fourier domain optical coherence tomography." *Optics Express* 12(24): 6033-6039.
Hitzenberger, et al., "Segmentation of the retinal pigment epithelium by polarization sensitive optical coherence tomography" Proc. of SPIE, Vol. 6847 684705:1-4
Pircher, et al., "Retinal pigment epithelium pathologies investigated with phase resolved polarization sensitive optical coherence tomography" Proc. of SPIE, Vol. 6138 61380I: 1-5

What is claimed is:

1. A method of generating an image of tissue using an optical coherence tomography (OCT) system, said OCT system including a light source generating a beam of light having an arbitrary polarization state, a sample arm and a reference arm and a detector for measuring light received from the sample and reference arms, said method comprising the steps of:
    (a) scanning the beam over the tissue to generate a first set of Z-axis intensity profiles at a plurality of X and/or Y positions of the beam;
    (b) varying the polarization state of the beam in one of the sample and reference arms using a polarization controller;
    (c) repeating steps (a) and (b) at least two more times to generate a a plurality of sets of Z-axis intensity profiles at a plurality of X and/or Y positions of the beam;
    (d) comparing the average intensity of the sets of Z-axis intensity profiles to identify two sets that have the highest and lowest average intensity difference;
    (e) combining intensity information at individual image sites from the two identified sets to provide information about the amount the tissue depolarizes the light without resolving the actual polarization state of the light and without passing the beam through a polarizer; and
    (f) displaying an image of the tissue which includes said depolarization information.

2. A method of generating an image as recited in claim 1, wherein said steps (a) and (b) are repeated at least four times.

3. A method of generating an image as recited in claim 2, wherein the highest and lowest intensity images are determined based on an average intensity across the entire image.

4. A method of generating an image as recited in claim 2, wherein the highest and lowest intensity images are determined based on an average intensity across a selected portion of the image.

5. A method of generating an image as recited in claim 4, wherein the selected portion corresponds to an anatomical feature within the eye.

6. A method of generating an image as recited in claim 1, wherein variations in hue in the image is used to represent the level of depolarization caused by the tissue.

7. A method of generating an image of eye tissue using an optical coherence tomography (OCT) system, said OCT system including a light source generating a beam of light having an arbitrary polarization state, a sample arm and a reference arm and a detector for measuring light received from the sample and reference arms, said method comprising the steps of:
    (a) scanning a region of the eye with the beam a plurality of times to generate intensity image information while using a polarization controller to vary the polarization state of the light within one of the sample and reference arms for each scan and wherein the beam is not passed through a polarizer;
    (b) comparing the intensity of the images derived from the scanning step at various locations across the image to identify two images that have different average intensities across the image;
    (c) combining the intensity information at individual image sites from the two identified images to provide information about the depolarization of tissue at each of those sites; and
    (d) displaying an image of the tissue which includes said depolarization information.

8. A method of generating an image as recited in claim 7, wherein the information about the amount the tissue depolarizes the light is determined without resolving the actual polarization state of the light.

9. A method of generating an image as recited in claim 7, wherein the step of scanning the eye and varying the polarization state of the light for each scan is repeated at least five times.

10. A method as recited in claim 9, wherein combining step is performed using two of the scans, said two scans corresponding respectively to the approximate highest and lowest average intensity images.

11. A method of generating an image as recited in claim 10, wherein the highest and lowest intensity images are determined based on an average intensity across the entire image.

12. A method of generating an image as recited in claim 10, wherein the highest and lowest intensity images are determined based on an average intensity across a selected portion of the image.

13. A method of generating an image as recited in claim 12, wherein the selected portion of the image corresponds to an anatomical feature within the eye.

14. A method of generating an image as recited in claim 7, wherein variations in hue in the image is used to represent the level of depolarization caused by the tissue.

15. A method of generating an image of eye tissue using an optical coherence tomography (OCT) system including a light source generating a beam of light having an arbitrary polarization, a sample arm and a reference arm, said method comprising the steps of:
(a) scanning the eye with a beam of light from the light source passing through the sample arm;
(b) collecting light reflected from eye;
(c) combining the collected light with light received from the reference arm on a single detector to generate image information, wherein the light is not passed through a polarizer;
(d) altering the polarization state of the light in one of the sample and reference arms using a polarization controller;
(e) repeating steps (a) through (d) at least five times;
(f) identifying the two images having respectively the approximate highest and lowest average intensity across the image;
(g) combining intensity information at individual image sites from the two identified images to provide information about the amount the tissue depolarizes the light without resolving the actual polarization state of the light; and
(h) displaying an image of the tissue which includes said depolarization information.

16. A method of generating an image as recited in claim 15, wherein the highest and lowest intensity images are determined based on an average intensity across the entire image.

17. A method of generating an image as recited in claim 15, wherein the highest and lowest intensity images are determined based on an average intensity across a selected portion of the image.

18. A method of generating an image as recited in claim 17, wherein the selected portion of the image corresponds to an anatomical feature within the eye.

19. A method of generating an image as recited in claim 15, wherein variations in hue in the image is used to represent the level of depolarization caused by the tissue.

20. A method of generating an image as recited in claim 15, wherein the detector is part of a spectrometer and is defined by an array of detector elements.

21. A method of generating an image of eye tissue using an optical coherence tomography (OCT) system, said OCT system including a light source generating a beam of light having an arbitrary polarization state, a sample arm and a reference arm and a detector for measuring light received from the sample and reference arms, said method comprising the steps of:
(a) scanning the same region of the eye with the beam a plurality of times while using a polarization controller to vary the polarization state of the light within one of the sample and reference arms for each scan and wherein the beam is not passed through a polarizer;
(b) comparing the images derived from the scanning step to identify two images that have the greatest average dissimilarity in intensities across the images;
(c) scanning the eye with the beam using the two polarization states associated with the two identified images;
(f) combining the intensity information at individual image sites obtained from the scans in step (c) to provide information about the depolarization of tissue at each of those sites; and
(g) displaying an image of the tissue which includes said depolarization information.

22. A method according to claim 21, where the location of the scans performed in steps (a) and (c) are performed in the same region of the eye.

23. A method according to claim 21, where the locations of the scans performed in step (a) are a subset of the locations of the scans performed in step (c).

24. A method according to claim 21, where images identified in step (b) correspond respectively to the average maximum and minimum intensity images.

25. An optical coherence tomography (OCT) system comprising:
a light source generating a beam of light having an arbitrary polarization state,
a sample arm, said sample arm including a scanner for scanning the beam over tissue;
a reference arm;
a polarization controller located in one of the sample and reference arms for varying the polarization state of the beam;
a detector for receiving light from the sample arm and the reference arm and generating intensity image information and wherein the beam is not transmitted through a polarizer; and
a processor for controlling the polarization controller in a manner to vary the polarization state of the beam, said processor for comparing average intensity image information across the image obtained at different polarization states and generating an image of the tissue based on the comparison that provide information about the depolarizing effects of the tissue.

26. A system as recited in claim 25 wherein the processor is arranged to generate a number of images and to select two of the images having the highest and lowest average intensity and using those two images to generate the image of the tissue that provides information about the depolarizing effects of the tissue.

27. A system as recited in claim 25 further including a display and for displaying images and wherein variations in hue are used to represent the level of depolarization caused by the tissue.

* * * * *

UNITED STATES PATENT AND TRADEMARK OFFICE
CERTIFICATE OF CORRECTION

PATENT NO.         : 8,208,996 B2                                    Page 1 of 1
APPLICATION NO.    : 12/381406
DATED              : June 26, 2012
INVENTOR(S)        : Scott A. Meyer et al.

It is certified that error appears in the above-identified patent and that said Letters Patent is hereby corrected as shown below:

On Title Page 2, Item (56), under Other Publications, Line 3, delete "613801-1-613801-5," and insert -- 613801-1 through 613801-5, --, therefor.

In column 9, line 59, after "1-5" insert -- . --.

In column 10, line 8, in Claim 1, after "generate" delete "a".

Signed and Sealed this
Twenty-fifth Day of September, 2012

David J. Kappos
*Director of the United States Patent and Trademark Office*